(12) United States Patent
Doty et al.

(10) Patent No.: US 7,722,555 B2
(45) Date of Patent: *May 25, 2010

(54) LOCKABLE HINGE

(75) Inventors: Alexis E. Doty, Carlsbad, CA (US); Richard E. Gildersleeve, Carlsbad, CA (US); Jennifer E. Sullivan, San Diego, CA (US)

(73) Assignee: DJO, LLC, Vista, CA (US)

( * ) Notice: Subject to any disclaimer, the term of this patent is extended or adjusted under 35 U.S.C. 154(b) by 100 days.

This patent is subject to a terminal disclaimer.

(21) Appl. No.: 11/768,868

(22) Filed: Jun. 26, 2007

(65) Prior Publication Data

US 2008/0077065 A1  Mar. 27, 2008

Related U.S. Application Data

(63) Continuation of application No. 10/242,372, filed on Sep. 11, 2002, now Pat. No. 7,235,058.

(51) Int. Cl.
*A61F 5/00* (2006.01)

(52) U.S. Cl. ............................. 602/16; 602/23; 602/27

(58) Field of Classification Search ................. 602/5, 602/16, 26, 27; 128/882
See application file for complete search history.

(56) References Cited

U.S. PATENT DOCUMENTS

| 401,933 | A | 4/1889 | De Camp |
|---|---|---|---|
| 2,832,334 | A | 4/1958 | Whitelaw |
| 3,826,251 | A | 7/1974 | Ross |
| 3,898,709 | A | 8/1975 | Lewis et al. |
| 4,088,130 | A | 5/1978 | Applegate |
| 4,337,764 | A | 7/1982 | Lerman |
| 4,340,041 | A | 7/1982 | Frank |
| 4,353,361 | A | 10/1982 | Foster |
| 4,463,751 | A | 8/1984 | Bledsoe |
| 4,489,718 | A | 12/1984 | Martin |
| 4,520,804 | A | 6/1985 | DiGeorge |

(Continued)

FOREIGN PATENT DOCUMENTS

EP   0466538 B1   6/1991

(Continued)

OTHER PUBLICATIONS http://www.townsenddesign.com/triggerlock.html, "Trigger Lock Hinge is versatile alternative to our Drop Lock Hinge", 2 pages, printed Jan. 9, 2003.

(Continued)

*Primary Examiner*—Michael A. Brown
(74) *Attorney, Agent, or Firm*—Ropes & Gray LLP (57) ABSTRACT

A lockable hinge for use in orthopedic braces is provided. When used in a knee brace, the present hinge provides a knee-immobilizing brace that assists persons with standing and/or walking. The hinge is easily converted from a locked mode to a free range of motion mode and vice versa. When the hinge is in the locked mode, patients are better able to stand and walk. With the push of a button, the patient can bend his or her knee to sit or lie down more comfortably. When the hinge is in the free range of motion mode, patients are better able to participate in physical therapy activities without the hinge locking.

9 Claims, 8 Drawing Sheets

U.S. PATENT DOCUMENTS

| | | | |
|---|---|---|---|
| 4,524,764 A | 6/1985 | Miller et al. | |
| 4,554,913 A | 11/1985 | Womack et al. | |
| D286,183 S | 10/1986 | Womack et al. | |
| 4,681,097 A | 7/1987 | Pansiera | |
| 4,732,143 A | 3/1988 | Kausek et al. | |
| 4,777,941 A | 10/1988 | Borig et al. | |
| 4,817,588 A * | 4/1989 | Bledsoe | 602/16 |
| 4,915,098 A * | 4/1990 | Young et al. | 602/16 |
| 4,982,732 A | 1/1991 | Morris | |
| 5,039,247 A | 8/1991 | Young et al. | |
| 5,042,464 A | 8/1991 | Skwor et al. | |
| 5,062,858 A | 11/1991 | Broeck et al. | |
| 5,063,917 A | 11/1991 | Young et al. | |
| 5,078,127 A | 1/1992 | Daneman et al. | |
| 5,107,824 A | 4/1992 | Rogers et al. | |
| 5,292,303 A | 3/1994 | Bastyr et al. | |
| 5,328,446 A | 7/1994 | Bunnell et al. | |
| 5,399,149 A | 3/1995 | Frankowiak et al. | |
| 5,399,154 A | 3/1995 | Kipnis et al. | |
| 5,409,449 A | 4/1995 | Nebolon | |
| 5,419,754 A | 5/1995 | Hutchins | |
| 5,443,444 A | 8/1995 | Pruyssers | |
| 5,630,791 A | 5/1997 | Glynn | |
| 5,676,640 A | 10/1997 | Biedermann | |
| 5,749,840 A | 5/1998 | Mitchell et al. | |
| 5,772,618 A * | 6/1998 | Mason et al. | 602/16 |
| 5,814,000 A | 9/1998 | Kilbey | |
| 5,885,235 A | 3/1999 | Opahle et al. | |
| 5,921,946 A | 7/1999 | Tillinghast et al. | |
| D416,624 S | 11/1999 | Nauert | |
| 5,997,493 A | 12/1999 | Young | |
| 6,004,283 A | 12/1999 | Young | |
| 6,039,709 A | 3/2000 | Bzoch | |
| 6,080,122 A | 6/2000 | Gulledge | |
| RE37,209 E * | 6/2001 | Hensley et al. | 602/26 |
| 6,375,632 B1 | 4/2002 | Albrecht et al. | |
| 6,387,066 B1 | 5/2002 | Whiteside | |
| 6,402,711 B1 * | 6/2002 | Nauert | 602/16 |
| 6,527,733 B1 * | 3/2003 | Ceriani et al. | 602/16 |

FOREIGN PATENT DOCUMENTS

| | | |
|---|---|---|
| EP | 0611093 A3 | 8/1994 |
| EP | 0761186 A2 | 3/1997 |
| EP | 0633007 B1 | 10/1997 |
| EP | 0832624 A2 | 4/1998 |
| EP | 0538695 B1 | 12/1998 |
| GB | 2235012 A | 2/1991 |
| GB | 2326098 A | 12/1998 |
| WO | WO 99/42071 | 8/1999 |
| WO | WO 01/10360 | 2/2001 |
| WO | WO 01/70149 A1 | 9/2001 |
| WO | WO 02/02037 A1 | 1/2002 |

OTHER PUBLICATIONS http://www.townsenddesign.com/specialty.html, "Specialty Braces: Custom braces designed for patients with severe instabilities and unique support requirements", 2 pages, printed Jan. 9, 2003.

Donjoy Bracing Catalogue, pp. 12-13, 1988.

Brochure from Flexgard, 1998.

Brace manufactured by dj Orthopedics, unlocked position, dated 1990.

Brace manufactured by dj Orthopedics, locked position, dated 1990.

* cited by examiner

LOCKABLE HINGE

CROSS REFERENCE TO RELATED APPLICATIONS

This application is a continuation of U.S. patent application Ser. No. 10/242,372, entitled "LOCKABLE HINGE," which was filed on Sep. 11, 2002 and is pending, and which is incorporated herein, in its entirety, by reference.

BACKGROUND OF THE INVENTION

1. Field of the Invention

The present invention relates to hinges for orthopedic braces. In particular, when used in combination with a knee brace, the present lockable hinge provides a locking mode to immobilize the knee joint, and a free range of motion mode for flexing the knee.

2. Description of the Related Art

Many people suffer from various instabilities that compromise their ability to ambulate and/or stand. These instabilities could include musculo-skeletal disorders such as quadriceps deficiencies, or neurological diseases such as muscular dystrophy, multiple sclerosis and polio. These instabilities interfere with the ability of the brain to properly control the muscle groups that are essential for ambulation and/or standing. As another example, people who have suffered strokes or spinal cord injuries also have difficulty controlling these muscle groups. For people who suffer from disorders such as these, walking and standing can be challenging or impossible. Bracing the person's leg so that he or she cannot bend his or her knee helps the person to stand and walk. A variety of leg braces that prevent knee flexion are available.

When sitting or lying down, generally a person is more comfortable if he or she can bend his or her knee. When wearing a knee-immobilizing brace, however, knee flexion is impossible. Thus, a person wearing such a brace must remove the brace whenever he or she sits or lies down. The process of removing the brace is difficult and time consuming. Furthermore, when the person wishes to stand up again, he or she needs to replace the brace on his or her leg. This process is also difficult and time consuming.

A hinge manufactured by Townsend Design and marketed under the name Trigger Lock enables a person to switch between a locked mode and an unlocked mode. In the locked mode, the hinge is freely rotatable between a first flexion angle and a second, maximum, flexion angle. When the hinge reaches a flexion angle less than the first flexion angle, the hinge automatically locks, such that the hinge cannot reach a flexion angle greater than the first flexion angle. By rotating a lever, the person can unlock the hinge so that the hinge can reach a flexion angle greater than the first flexion angle. By rotating a second lever, the person can place the hinge in the unlocked mode. In the unlocked mode the hinge is freely rotatable and does not lock when it reaches a flexion angle less than the first flexion angle.

A hinge manufactured by dj Orthopedics of Vista, Calif., and described in U.S. Pat. Nos. 5,292,303 and 5,409,449 also enables a person to switch between a locked mode and an unlocked mode. The hinge includes a lever that protrudes in a substantially radial direction. A spring biases the lever toward a locked position in which the lever interferes with rotation of the hinge arms. When the lever is in the locked position, the hinge is locked at full extension. The lever is movable to an unlocked position in which the lever does not interfere with rotation of the hinge arms. When the lever is in the unlocked position, the hinge is freely rotatable between full extension and approximately 120° of flexion. A latch secured to an edge of the hinge plates is selectively engageable with the lever to hold the lever in the unlocked position. When the hinge is oriented at any angle short of full extension, and the latch is disengaged from the lever, the lever is biased toward the locked position. However, one of the hinge arms obstructs the lever, preventing the lever from reaching the locked position. When the hinge reaches full extension, the hinge arm no longer obstructs the lever, and the lever snaps into the locked position.

The hinge further includes a flexion-limiting pin and an extension-limiting pin. The pins are selectively engageable with a plurality of apertures on the hinge plates to set ranges of flexion and extension for the hinge. Thus, using the pins a wearer may lock the hinge at full extension by appropriately positioning the pins to prevent flexion.

Another hinge manufactured by dj Orthopedics also enables a person to switch between a locked mode and an unlocked mode. However, the hinge does not lock automatically upon reaching a pre-determined flexion angle. Rather, the hinge includes a two-position switch that is slidable in the anterior/posterior direction. When the switch is in the posterior position, the hinge is freely rotatable between full extension and approximately 120° of flexion. When the hinge is at full extension, the wearer may slide the switch to the anterior position, where the switch locks the hinge at full extension.

Another hinge manufactured by dj Orthopedics, and described in U.S. Pat. No. 5,921,946 also enables a person to switch between a locked mode and an unlocked mode. This hinge also does not lock automatically upon reaching a pre-determined flexion angle. One of the hinge plates includes a locking switch that is slidable toward and away from the other hinge plate. When the switch is slid toward the opposite hinge plate, it engages one of a plurality of slots on the opposite hinge plate, preventing rotation of the hinge. The slots are positioned such that the hinge may be locked at a plurality of different angles of flexion, including full extension. When the switch is slid away from the opposite hinge plate, it disengages the slot and the hinge becomes freely rotatable. The hinge further includes an extension-limiting stop and a flexion-limiting stop. Each stop is slidable between a plurality of positions to set a maximum extension/flexion range for the hinge. In each position, each stop engages a different land on one of the hinge plates to define the extension/flexion limit.

SUMMARY OF THE INVENTION

The preferred embodiments of the lockable hinge have several features, no single one of which is solely responsible for their desirable attributes. Without limiting the scope of this lockable hinge as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include easy conversion between a locked mode and a free range of motion mode, thus eliminating the need to remove and reapply a brace into which the hinge is incorporated.

A preferred embodiment of the present lockable hinge comprises a lockable hinge for use in an orthopedic brace. The hinge comprises a hinge plate, an arm rotatably mounted to the hinge plate, the arm being rotatable about a hinge axis, and a flexion stop. The flexion stop is movable in a direction substantially parallel to the hinge axis between a first position in which the flexion stop limits a range of flexion of the arm, and a second position in which the flexion stop does not limit a range of flexion of the arm.

When the arm occupies a first flexion range, the arm preferably maintains the flexion stop in the first position. When the arm occupies a second flexion range, the arm preferably does not maintain the flexion stop in the first position. When the arm occupies the second flexion range, a flexion abutment face on the arm preferably cooperates with a flexion abutment face on the flexion stop to limit a range of flexion of the hinge.

The lockable hinge may further comprise a toggle that is selectively engageable with the flexion stop. When the toggle does not engage the flexion stop, preferably the flexion stop moves toward the second position when the arm occupies the second flexion range. When the toggle engages the flexion stop, preferably the flexion stop remains in the first position when the arm occupies the second flexion range.

The lockable hinge may further comprise a second arm rotatably mounted to the hinge plate, the second arm being rotatable about a second hinge axis. The lockable hinge may further comprise an extension stop.

Another preferred embodiment of the present lockable hinge comprises a lockable hinge for an orthopedic brace. The hinge comprises a hinge plate having a first aperture defining a first hinge axis and a second aperture defining a second hinge axis. A first arm is secured to the hinge plate such that the first arm is rotatable about the first hinge axis. A second arm is secured to the hinge plate such that the second arm is rotatable about the second hinge axis. The hinge further comprises a flexion stop. The flexion stop is selectively positionable within a recess in the hinge plate, but is biased outward of the recess, such that when the arms occupy a first flexion range the arms maintain the flexion stop within the recess, enabling the arms to reach a first maximum flexion angle, and when the arms occupy a second flexion range the flexion stop is expelled from the recess and limits the arms to a second maximum flexion angle that is less than the first maximum flexion angle.

The hinge may further comprise a second hinge plate. Preferably, the flexion stop comprises a plate-like portion and a protruding portion. A cross-section of the protruding portion is preferably shaped substantially as a tear drop. The protruding portion may comprise a button. A portion of the button preferably protrudes through an aperture in the second hinge plate. A toggle is preferably mounted to an outer surface of the second hinge plate. The toggle is preferably selectively engageable with the portion of the button that protrudes from the second hinge plate. When the toggle engages the button, the toggle preferably maintains the flexion stop within the recess. The toggle preferably includes a depression for receiving the button. The toggle preferably further includes at least one sloped surface adjacent the depression. The toggle may be pivotably mounted to the second hinge plate. When the button is disposed in the depression, the button preferably prevents the toggle from rotating. The toggle preferably further comprises a through-hole that enables access to the button when the toggle engages the button. The toggle is preferably pivotably mounted to the second hinge plate. The toggle may be pivotably mounted to the second hinge plate with a rivet.

The toggle preferably further comprises a groove. The groove is preferably selectively engageable with the button. The groove may be V-shaped. The button preferably includes a hollow interior portion. The button hollow interior portion preferably receives a spring. The spring preferably receives a post located in the recess such that the flexion stop is movable with respect to the post and biased away from the post.

Ends of the arms are preferably located between the first and second hinge plates. The arms may be secured to at least one of the first and second hinge plates with rivets. The hinge may further comprise a friction-reducing bearing plate disposed between the arms and at least one of the first and second hinge plates. The hinge preferably further comprises an extension stop secured to the hinge plate. The arms may be secured to the hinge plate with rivets. A first end of each arm preferably includes gear teeth, and the gear teeth of the first arm intermesh with the gear teeth of the second arm such that the arms cannot rotate independently of one another.

Another preferred embodiment of the present lockable hinge comprises a lockable hinge for an orthopedic brace. The hinge comprises first and second hinge arms rotatably mounted to a hinge plate. The hinge further comprises a flexion stop movable between a first position and a second position, and biased toward the second position. When the flexion stop is in the first position and the hinge reaches a pre-determined angle of extension, the flexion stop moves from the first position to the second position.

Preferably, when the flexion stop is in the first position, the flexion stop does not limit a maximum flexion angle of the hinge. Preferably, when the flexion stop is in the second position, the flexion stop limits a maximum flexion angle of the hinge. The flexion stop is preferably movable from the second position to the first position.

The hinge preferably further comprising a toggle. The toggle is preferably selectively engageable with a protrusion secured to the flexion stop to lock the flexion stop in the first position. When the flexion stop is locked in the first position, the flexion stop preferably is not permitted to move from the first position to the second position when the hinge reaches the pre-determined angle of extension.

The hinge preferably further comprises an extension stop limiting an extension angle of the hinge. The hinge may further comprise a friction-reducing bearing plate situated between the hinge plate and the first and second arms. The hinge may further comprise a second hinge plate such that ends of the arms are situated between the first and second hinge plates.

Another preferred embodiment of the present lockable hinge comprises a method of assisting a person with standing and/or walking. The method comprises the steps of beginning from a seated position with a knee bent, unbending the knee to straighten a leg to an extended position, locking a hinge incorporated in a knee brace secured to the leg, such that the locked hinge limits the knee to a maximum flexion angle, and rising from the seated position to a standing position. The locking step comprises disengaging a toggle from a protrusion on a flexion stop.

The method may further comprise the step of moving the flexion stop from a first position to a second position, wherein when the flexion stop is in the first position it does not limit the knee to a maximum flexion angle, and when the flexion stop is in the second position it limits the knee to a maximum flexion angle. Preferably, when the flexion stop is in the first position it is contained within a recess in a hinge plate of the hinge, and when the flexion stop is in the second position it is expelled from the recess.

The method may further comprise the step of walking. The method may further comprise the step of returning to the seated position. The method may further comprise the step of depressing the protrusion on the flexion stop, thereby moving the flexion stop from the second position to the first position, and engaging the toggle with the protrusion on the flexion stop, thereby locking the flexion stop in the first position.

BRIEF DESCRIPTION OF THE DRAWINGS

The preferred embodiments of the lockable hinge, illustrating its features, will now be discussed in detail. These embodiments depict the novel and non-obvious lockable hinge shown in the accompanying drawings, which are for illustrative purposes only. In the descriptions of these embodiments, all directional references are made with respect to the body of the lockable hinge wearer. Thus, a top/bottom view refers to a view along a superior/inferior axis, a side view refers to a view along a medial/lateral axis, and a front/rear view refers to a view along an anterior/posterior axis. Further, the illustrated embodiments of the lockable hinge could be worn on either the lateral side of the left knee or the medial side of the right knee. For ease of reference, however, the lockable hinge will be described herein as if worn on the lateral side of the left knee. Those of skill in the art will appreciate that a mirror image of the illustrated lockable hinge could be adapted for wear on either the medial side of the left knee or the lateral side of the right knee. In a preferred embodiment, a knee brace including the present lockable hinge has one hinge on each side of a wearer's knee. The drawings of the lockable hinge include the following figures, in which like numerals indicate like parts.

DETAILED DESCRIPTION OF THE PREFERRED EMBODIMENTS

The present lockable hinge 20, illustrated in FIGS. 1-8D, has a broad range of applications in orthopedic bracing. One such application is in a knee brace that assists people who suffer from musculo-skeletal or neurological disorders that compromise their ability to ambulate and/or stand. For example, a doctor may recommend a knee brace including the present lockable hinge 20 for polio patients or patients who have suffered spinal cord injuries. Such patients may have difficulty controlling the muscle groups that are essential for walking and standing upright. A brace including the present lockable hinge 20 enables the patient to walk and stand by reducing the patient's need to rely on certain muscles. For ease of reference, the present lockable hinge 20 will be described with reference to such a patient. Those of skill in the art will appreciate, however, that the present lockable hinge 20 is useful for a variety of other applications. Therefore, the description below should not be interpreted as limiting the present lockable hinge 20 to one application.

With reference to FIGS. 1-6, the lockable hinge 20 comprises a first arm 22 and a second arm 24, each of which is pivotably secured between a first hinge plate 26 and a second hinge plate 28. The first arm 22 is pivotable at a first end 30 (FIG. 5) about a first hinge axis 34 that is substantially perpendicular to the hinge plates 26, 28. The second arm 24 is pivotable at a first end 32 about a second hinge axis 36 that is spaced from and substantially parallel to the first hinge axis 34. Preferably the hinge 20 includes a lateral bearing plate 38 situated between the arms 22, 24 and the second hinge plate 28, and a medial bearing plate 40 situated between the arms 22, 24 and the first hinge plate 26. The bearing plates 38, 40 are constructed of a low-friction material, such as nylon or Delrin®, that facilitates rotation of the arms 22, 24 between the hinge plates 26, 28. Those of skill in the art will appreciate that the bearing plates 38, 40 need not be provided.

When the hinge 20 is used in combination with a knee brace (not shown), the first arm 22 corresponds to a first upright (not shown) that extends along the wearer's thigh, and the second arm 24 corresponds to a second upright (not shown) that extends along the wearer's lower leg. Each arm 22, 24 preferably includes, near a second end spaced from the first end 30, 32, a pair of apertures 42 (FIG. 1) that cooperate with fasteners to secure each arm 22, 24 to its respective upright. Those of skill in the art will appreciate that the arms 22, 24 need not include the apertures 42. Those of skill in the art will also appreciate that the uprights may be integrally connected to the hinge 20, rather than secured to the arms 22, 24. For example, each arm 22, 24 may extend along the wearer's leg and include apparatus for securing the arms 22, 24 to the wearer's leg.

Figure 5:
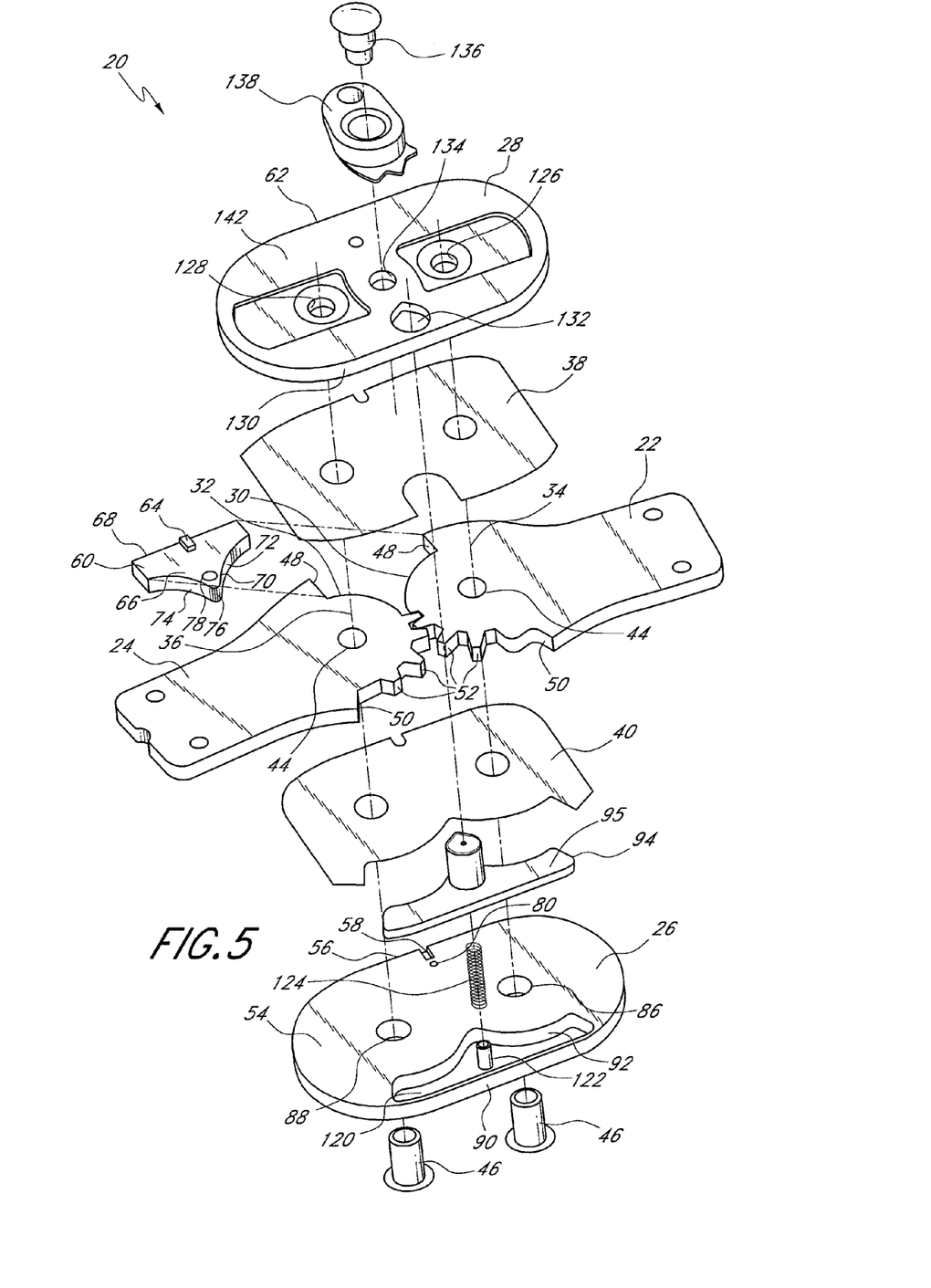
FIG. 5 is an exploded perspective view of the lockable hinge of FIG. 1 taken from a posterior side of the hinge.
Figure 6:
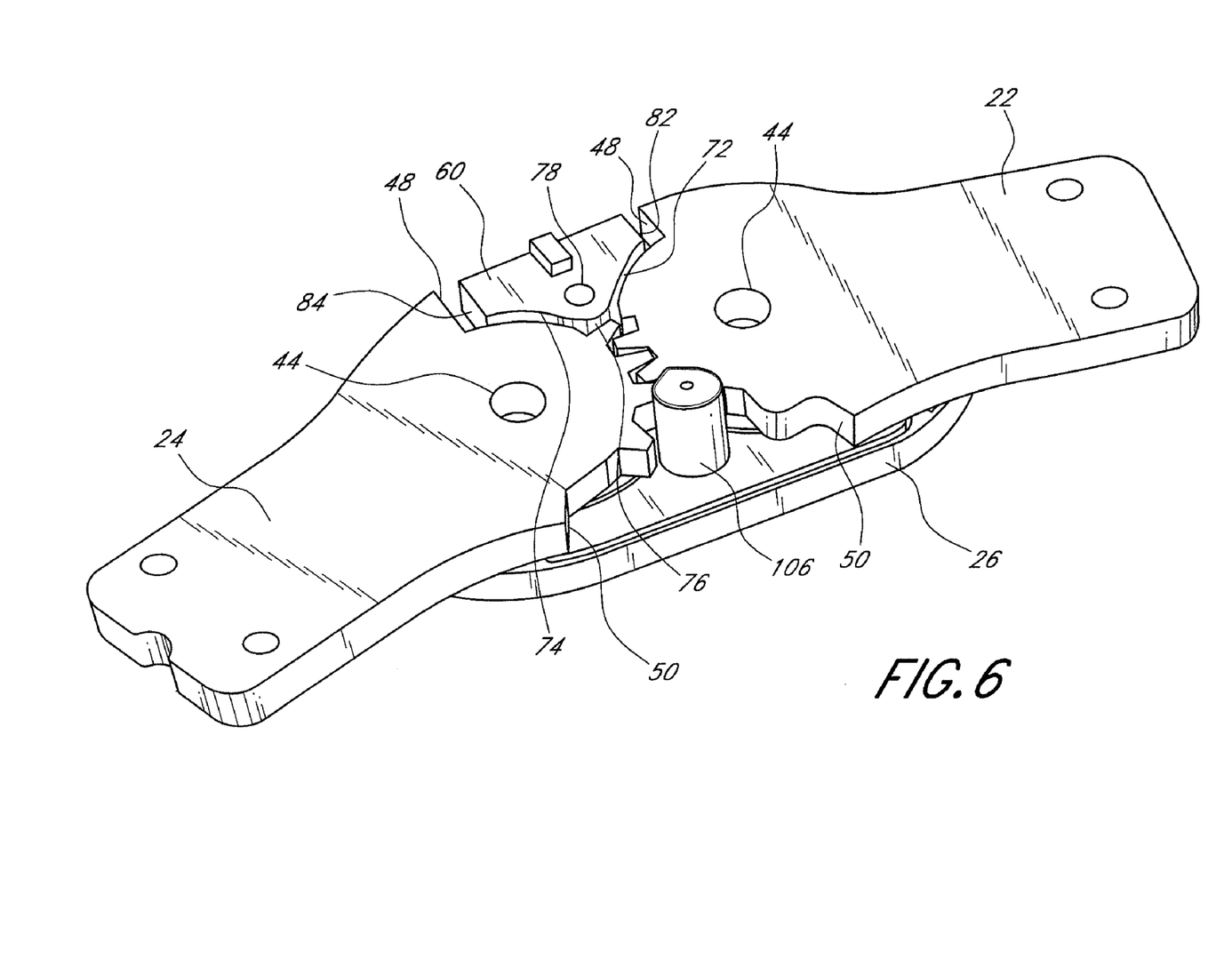
FIG. 6 is a perspective view of the lockable hinge of FIG. 1, with the lateral hinge plate removed, taken from a posterior side of the hinge.

Each arm 22, 24 includes, adjacent the first end 30, 32 of each, a through-hole 44 (FIGS. 5 and 6). Each through-hole 44 cooperates with a fastener 46 (FIGS. 1 and 5) to pivotably secure the respective arm 22, 24 to the hinge plates 26, 28. In the illustrated embodiment, the fasteners 46 comprise rivets. However, those of skill in the art will appreciate that the fasteners 46 could also comprise, for example, bolts, screws, or other similar fasteners.

Each arm first end 30, 32 further comprises an extension abutment face 48 and a flexion abutment face 50 (FIGS. 5 and 6). Each arm first end 30, 32 may further comprise a plurality of gear teeth 52 intermediate the abutment faces 48, 50. The gear teeth 52 on each arm 22, 24 preferably intermesh with the gear teeth 52 on the opposite arm 22, 24. The arms 22, 24 thus cannot rotate independently of one another, which results in smoother operation of the hinge 20 during knee flexion and extension. Those of skill in the art will appreciate that the gear teeth 52 need not be provided, and that without the gear teeth 52 the arms 22, 24 would be capable of rotating independently of one another.

A portion of a lateral face 54 (FIG. 5) of the first hinge plate 26 adjacent an anterior edge 56 thereof includes a groove 58. A ridge (not shown) on a medial face (not shown) of an extension stop 60 (FIGS. 5 and 6) rests in the groove and secures the extension stop 60 to the first hinge plate 26. A portion of the medial face (not shown) of the second hinge plate 28 adjacent an anterior edge 62 (FIG. 5) thereof also includes a groove (not shown). A ridge 64 on a lateral face 66 (FIG. 5) of the extension stop 60 rests in the groove and secures the extension stop 60 to the second hinge plate 28.

The extension stop 60 preferably includes a substantially straight anterior edge 68 corresponding to the anterior edge 56 of the first hinge plate 26 (FIG. 5). A posterior edge 70 of the extension stop 60 preferably includes first and second adjacent interior curved portions 72, 74 that intersect at a crest 76 (FIGS. 5 and 6). The first curved portion 72 lies adjacent the first end 30 of the first arm 22, and the second curved portion 74 lies adjacent the first end 32 of the second arm 24. A radius of each curved portion 72, 74 is preferably slightly larger than an outer radius of the gear-toothed portions 52 of the first and second arms 22, 24. The curved portions 72, 74 thus provide clear rotation paths for the first ends 30, 32 of the first and second arms 22, 24.

The extension stop 60 preferably includes at least one aperture 78 for receiving a fastener (not shown) such as a screw. The screw cooperates with a threaded hole 80 (FIG. 5) in the first hinge plate 26 to secure the extension stop 60 to the first hinge plate 26. In the illustrated embodiment, the aperture 78 is located adjacent the crest 76. Those of skill in the art will appreciate that the aperture 78 may be located anywhere on the extension stop 60. Those of skill in the art will further appreciate that the extension stop 60 may include more than one aperture 78, or may not include any aperture 78. For example, the extension stop 60 may be glued to the first hinge plate 26. The extension stop 60 may also be secured to the second hinge plate 28 with mechanical fasteners or by gluing, for example.

A superior end of the extension stop 60 includes a first abutment face 82 (FIG. 6) that is selectively engageable with the extension abutment face 48 on the first arm 22 to limit an extension range of the first arm 22. Similarly, an inferior end of the extension stop 60 includes a second abutment face 84 that is selectively engageable with the extension abutment face 48 on the second arm 24 to limit an extension range of the second arm 24. In the illustrated embodiment, the extension stop 60 limits extension of the hinge 20 to approximately 10°. Those of skill in the art will appreciate that a variety of other extension stops could be provided to limit the hinge 20 to greater or lesser extension. For example, as a patient progresses through a prescribed course of treatment, he or she may be better able to extend his or her knee. Thus, at an advanced stage of the treatment, a physician may remove the extension stop and replace it with one allowing greater extension.

In the illustrated embodiment, the first hinge plate 26 is substantially oval-shaped in side elevation aspect. The first hinge plate 26 includes a pair of apertures 86, 88 (FIG. 5) corresponding to the first and second hinge axes 34, 36. The apertures 86, 88 preferably lie substantially along a longitudinal axis of the first hinge plate 26, and are substantially evenly spaced from a midpoint of the first hinge plate 26 as measured along the longitudinal axis. The fasteners 46 cooperate with these apertures 86, 88 to secure the arms 22, 24 to the first hinge plate 26.

Figure 7A:
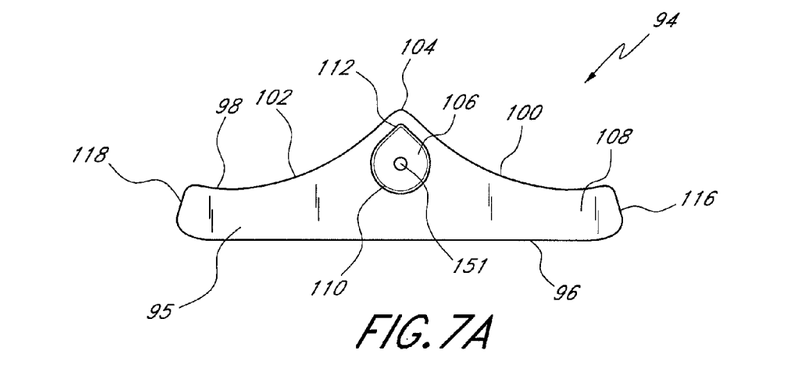
FIG. 7A is a side view of the flexion stop of the lockable hinge of FIG. 1.

A portion of the lateral face 54 of the first hinge plate 26 adjacent a posterior edge 90 thereof includes a recess 92 for selectively housing a flexion stop 94 (FIGS. 5 and 7A-7C). The flexion stop 94 includes a substantially plate-like portion 95 (FIGS. 7A and 7B), having a thickness that is preferably substantially equal to a thickness of the arms 22, 24. A posterior edge 96 of the flexion stop 94 is preferably substantially straight and lies adjacent the posterior edge 90 of the first hinge plate 26 (FIGS. 5 and 7A-7C). An anterior edge 98 (FIGS. 7A and 7C) of the flexion stop 94 preferably includes first and second adjacent interior curved portions 100, 102 that intersect at a crest 104 (FIG. 7A).

As illustrated in FIG. 6, the first curved portion 100 lies adjacent the gear teeth 52 on the first end 30 of the first arm 22. The second curved portion 102 lies adjacent the gear teeth 52 on the first end 32 of the second arm 24. A radius of each curved portion 100, 102 is preferably slightly larger than an outer radius of the gear-toothed portions 52 of the first and second arms 22, 24. The curved portions 100, 102 thus provide clear rotation paths for the first ends 30, 32 of the first and second arms 22, 24.

A substantially cylindrical button 106 (FIGS. 7A-7C) protrudes from a lateral face 108 of the flexion stop 94. In the illustrated embodiment, a transverse cross-section of the button 106 is not perfectly round. Rather, the cross-section is shaped substantially as a water droplet, including a rounded portion 110 and a crest 112 (FIG. 7A). Those of skill in the art will appreciate that the button 106 could have a round cross-section, or any other geometric or irregular shape. The button 106 preferably includes a substantially cylindrical hollow interior portion 114 (FIG. 7C). The button 106 enables a wearer to release the lockable hinge 20 from a locked configuration, as described below.

A superior edge of the flexion stop 94, which forms an angle of approximately 85° with the posterior edge 96, comprises a first abutment face 116 (FIG. 7A) that is selectively engageable with the flexion abutment face 50 on the first arm 22 to limit a flexion range of the first arm 22. Similarly, an inferior edge of the flexion stop 94, which forms an angle of approximately 85° with the posterior edge 96, comprises a second abutment face 118 (FIG. 7A) that is selectively engageable with the flexion abutment face 50 on the second arm 24 to limit a flexion range of the second arm 24. Thus, when the flexion stop abutment faces 116, 118 engage the flexion abutment faces 50 on the first and second arms 22, 24, the flexion stop 94 limits flexion of the hinge 20 to approximately 10°. Those of skill in the art will appreciate that more or less flexion may be provided by altering the angle at which each flexion stop abutment face 116, 118 intersects the flexion stop posterior edge 96.

Figure 2:
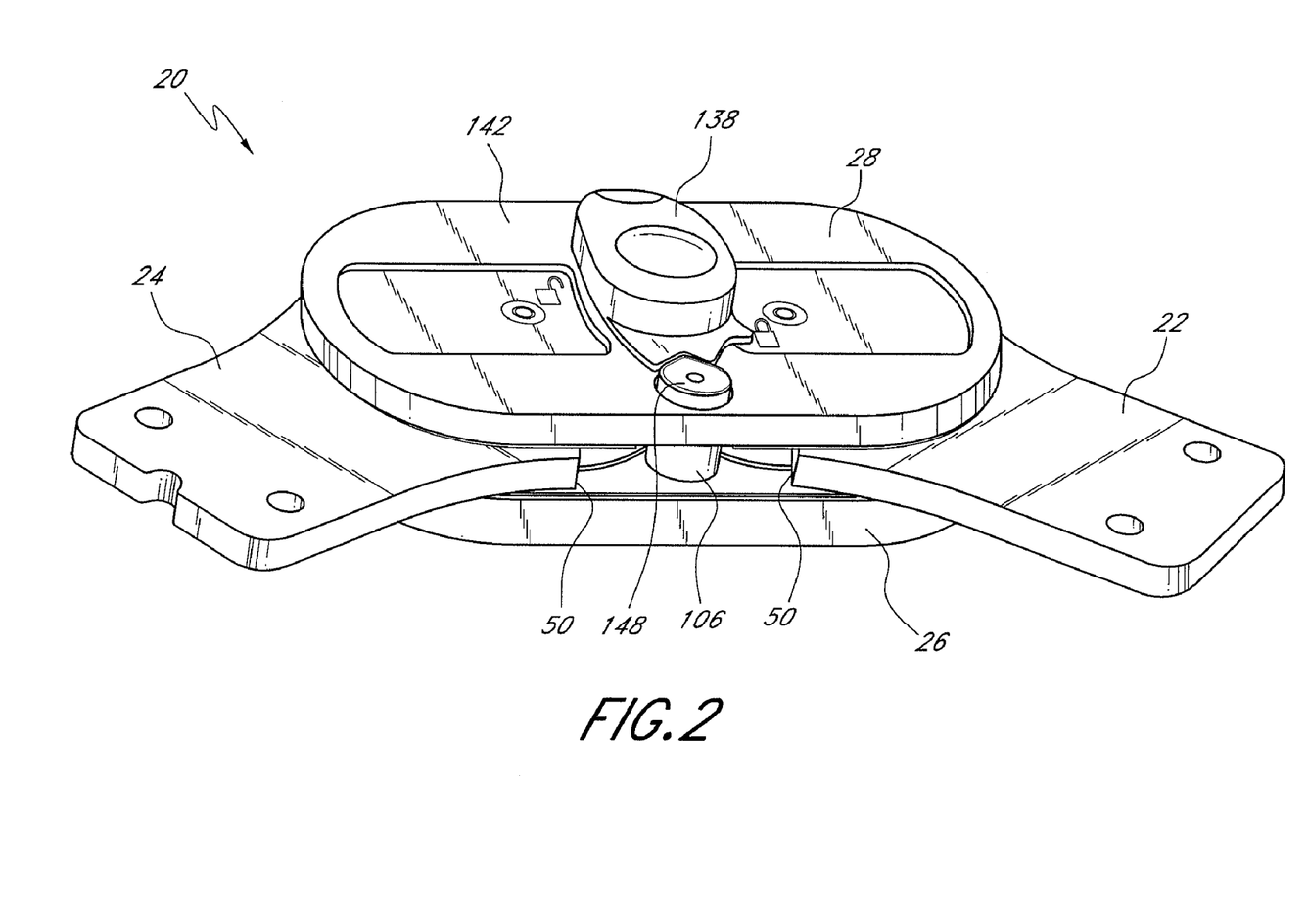
FIG. 2 is a perspective view of the lockable hinge of FIG. 1 taken from a posterior side of the hinge.
Figure 4:
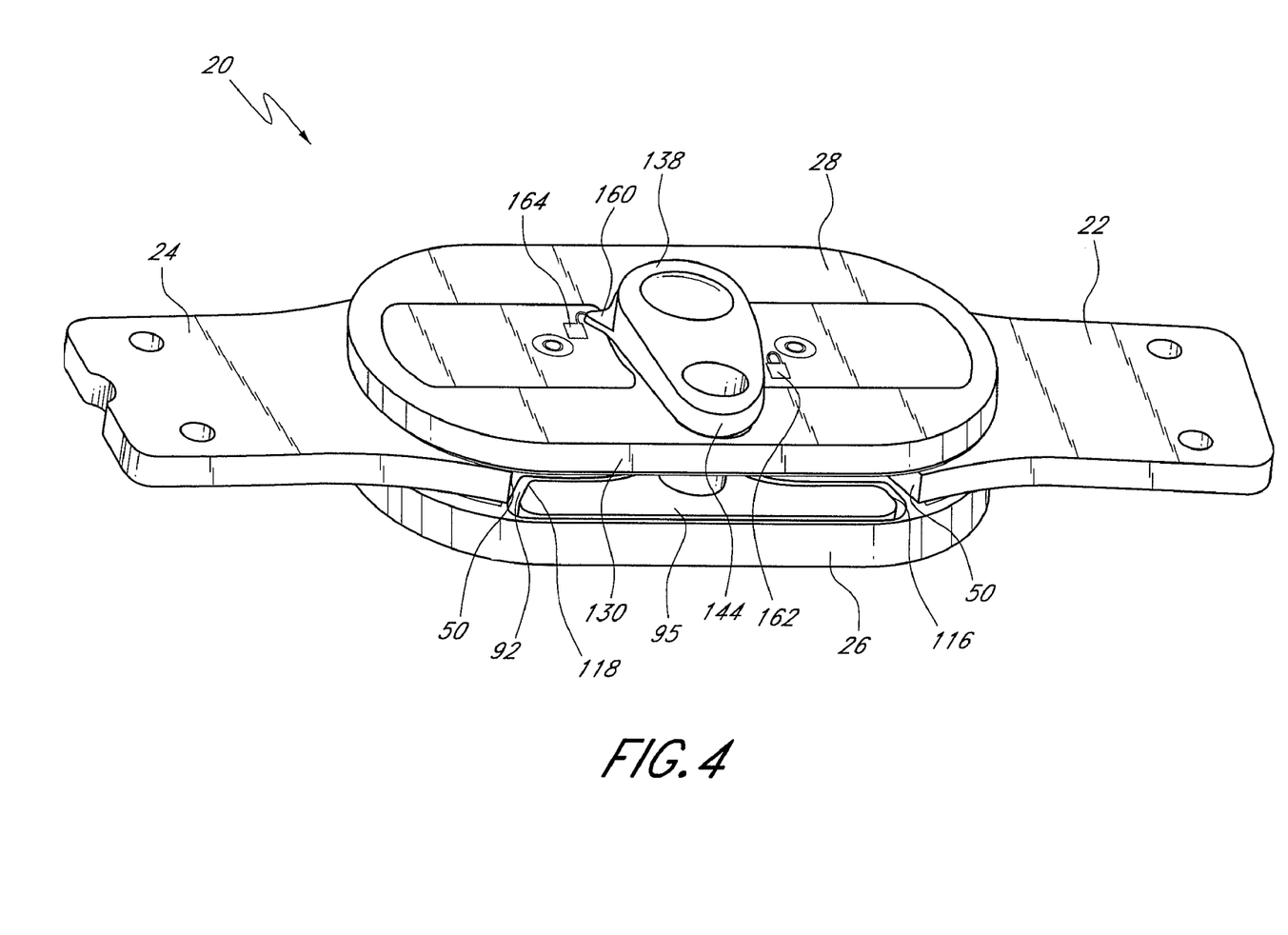
FIG. 4 is a perspective view of the lockable hinge of FIG. 1 taken from a posterior side of the hinge.

A perimeter of the recess 92 in the lateral face 54 of the first hinge plate 26 is preferably of substantially the same shape as, but slightly larger than, the perimeter of the flexion stop 94 (FIG. 5). A depth of the recess 92 is preferably slightly larger than the thickness of the flexion stop plate-like portion 95. The recess 92 is thus capable of housing the flexion stop plate-like portion 95 such that the plate-like portion 95 does not protrude above the lateral face 54 of the first hinge plate 26, as shown in FIGS. 2, 4 and 6. A floor 120 of the recess 92 includes a post 122 (FIG. 5) that receives a medial end of coil spring 124. A lateral end of the coil spring 124 extends into the hollow interior portion 114 of the button 106. The flexion stop 94 is thus movable into and out of the recess 92 as the coil spring 124 recoils and expands around the post 122. The coil spring 124 biases the flexion stop 94 out of the recess 92.

Figure 1:
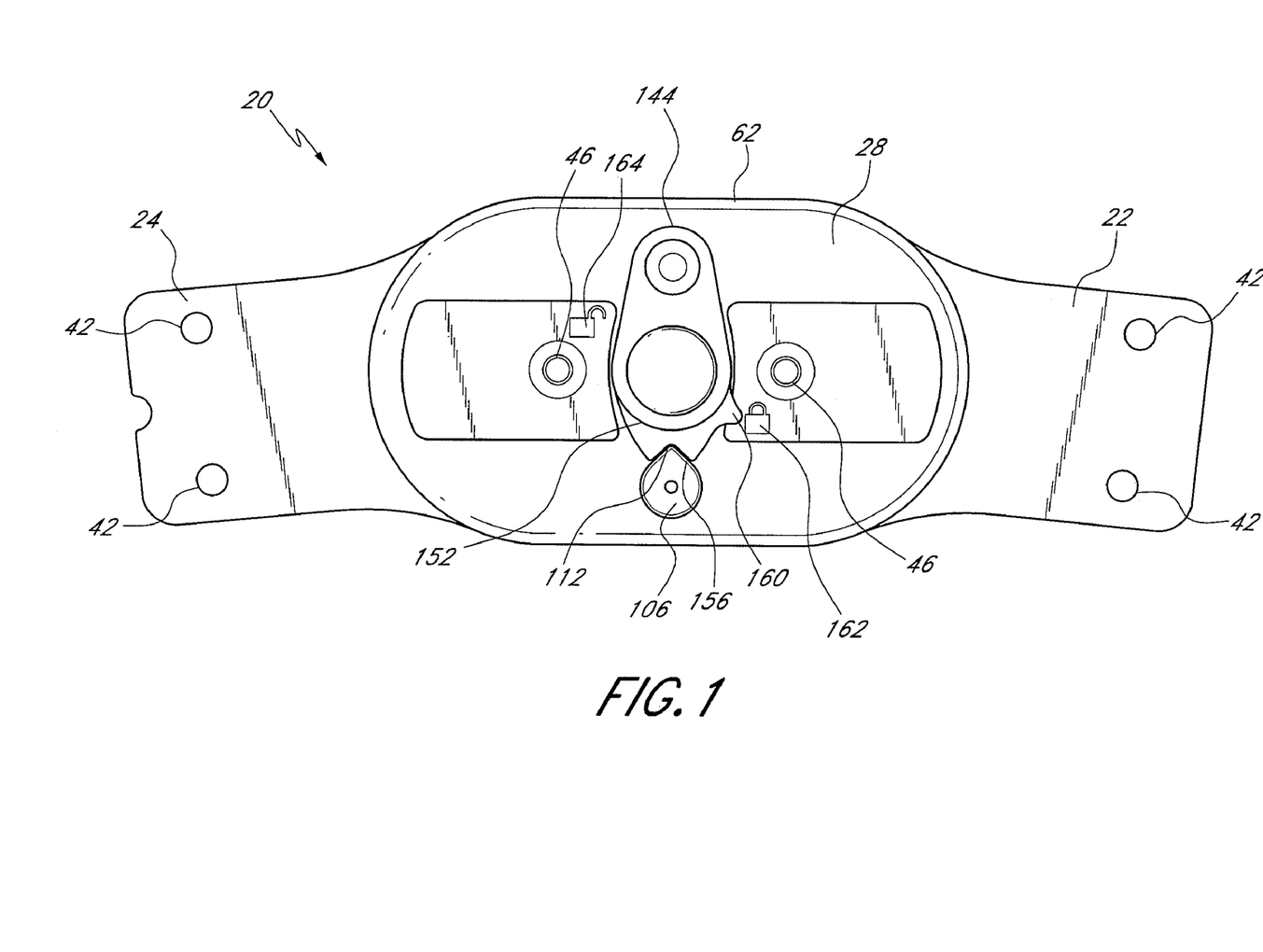
FIG. 1 is a side view of a preferred embodiment of the present lockable hinge taken along a medial/lateral axis.

The second hinge plate 28 is substantially oval-shaped in side-elevation aspect (FIG. 1). The second hinge plate 28 includes first and second apertures 126, 128 (FIG. 5) corresponding to the first and second hinge axes 34, 36. The first and second apertures 126, 128 cooperate with the fasteners 46 to secure the second hinge plate 28 to the hinge 20. Adjacent a posterior edge 130 (FIG. 5), the second hinge plate 28 includes a third aperture 132 through which the button 106 protrudes. Near a center, the second hinge plate 28 includes a fourth aperture 134 (FIG. 5) that receives a fastener 136 such as a rivet.

A toggle 138 (FIGS. 5 and 8A-8D) is pivotably mounted to the fastener 136. The toggle 138 is a substantially oblong switch having a first through hole 139 (FIGS. 8C and 8D) for receiving the fastener 136. The toggle 138 preferably has a substantially flat medial surface 140 (FIGS. 8A, 8C and 8D) that abuts a lateral face 142 (FIG. 5) of the second hinge plate 28. The toggle 138 is pivotable 360° about the fastener 136.

However, as those of skill in the art will appreciate, the toggle may be rotatable less than 360°. The toggle 138 may also be mounted to the second hinge plate 28 in alternative fashions. For example, the toggle 138 may be slidable with respect to the second hinge plate 28.

A first end 144 (FIGS. 8A, 8C and 8D) of the toggle 138, spaced from the fastener 136, engages the button 106 when the toggle 138 is rotated such that the first end 144 is adjacent the posterior edge of the second hinge plate 28, as shown in FIG. 4. In this position, the toggle 138 retains the button 106 in a depressed position, which urges the plate-like portion 95 into the recess 92. When the plate-like portion 95 is in the recess 92, the flexion abutment faces 116, 118 on the flexion stop 94 do not interfere with the flexion abutment faces 50 on the arms 22, 24. The arms 22, 24 are thus free to rotate between a maximum extension, wherein the extension abutment faces 82, 84 (FIG. 6) on the extension stop 60 abut the extension abutment faces 48 on the arms 22, 24, and a maximum flexion, wherein the flexion abutment faces 50 (FIG. 6) on the arms 22, 24 abut the button 106. This configuration defines a free range of motion for the hinge 20. Preferably, the free range of motion of the hinge 20 is between 10° short of full extension and 125° of flexion. However, those of skill in the art will appreciate that the hinge could have a free range of motion between a variety of different extension and flexion limits.

Advantageously, the button 106 always protrudes above the lateral face 142 (FIGS. 2 and 3) of the second hinge plate 28 unless the wearer manually depresses the button 106. The button 106 thus prevents the hinge 20 from accidentally entering the free range of motion mode. If the toggle 138 were to accidentally rotate such that the first end 144 approached the button 106, the toggle 138 would contact a side of the button 106. The toggle 138 could not ride over the button 106 and place the hinge in the free range of motion mode.

Adjacent the first end 144, the medial surface 140 of the toggle 138 preferably includes a depression 146 (FIGS. 8B, 8C and 8D) that is substantially the same size and shape as a cross-section of the button 106. When the toggle 138 is in the free range of motion position as pictured in FIG. 4, a short length of the lateral end 148 (FIGS. 2 and 7B) of the button 106 is disposed within the depression 146. The button 106 thus locks the toggle 138 in this position.

Adjacent the first end 144, the toggle 138 preferably includes a second through-hole 150 (FIGS. 8B, 8C and 8D) that is substantially centered on the depression 146, but has a shorter perimeter to prevent the button from entering the second through-hole 150. In order to unlock the toggle 138 from the free range of motion position of FIG. 4, the wearer inserts a slender object, such as a straightened paper clip or the point of a pen, through the hole 150, depressing the button 106 while at the same time rotating the toggle 138. Once the button 106 clears the depression 146, the toggle 138 can be rotated freely.

Preferably, the perimeter of the second through-hole 150 is short enough that objects cannot accidentally enter the second through-hole 150 and depress the button 106, which might accidentally unlock the toggle 138 from the free range of motion position of FIG. 4. The lateral end 148 (FIGS. 7A and 7C) of the button 106 preferably includes an indentation 151 near a center thereof. The indentation 151 guides the object that the wearer inserts and enable smooth operation of the button 106 by reducing a tendency for the object to slide across the button 106 as the wearer applies a pushing force. Those of skill in the art will appreciate that the indentation 151 need not be provided.

The flexion stop 94 may include a second button (not shown) protruding from the plate-like portion 95 in substantially the same direction as the button 106 and spaced from the button 106. The second button would preferably extend above the surface of the second hinge plate 28, but would preferably not engage the toggle 138. To engage the toggle 138 and the button 106, and also to disengage those two components, the wearer would depress the second button and hold it down while rotating the toggle 138. While engaging the toggle 138 with the button 106, the wearer's finger would not interfere with the toggle 138. While disengaging the toggle 138 from the button 106, the wearer would not need to use a separate tool to depress the button 106. Preferably the second button would not interfere with rotation of the arms 22, 24. For example, the second button could be positioned posteriorly of the button 106. If the second button were positioned superiorly of the button 106, the arm 22 could include a slot (not shown) for receiving the second button as the arm 22 rotated.

Figure 3:
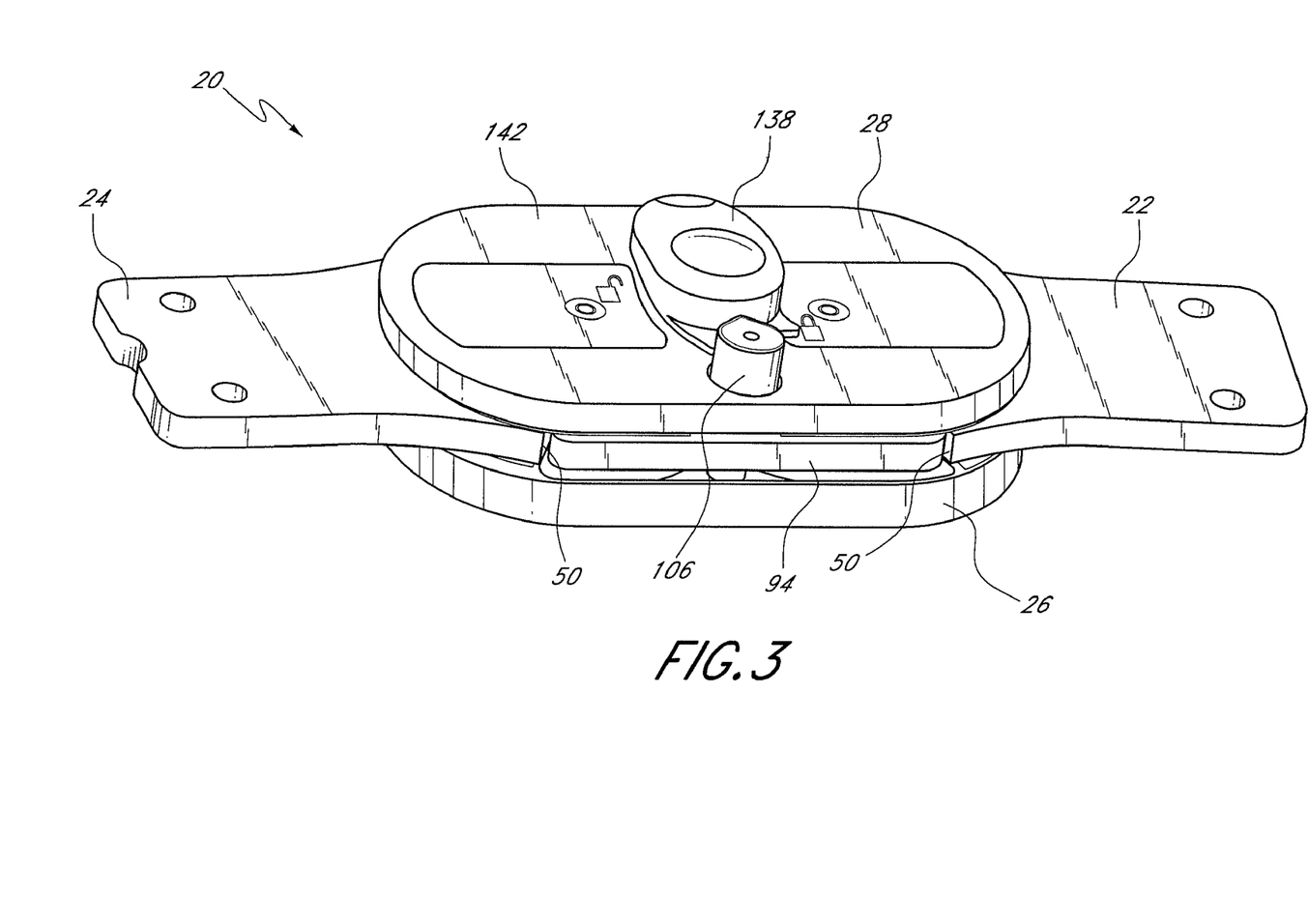
FIG. 3 is a perspective view of the lockable hinge of FIG. 1 taken from a posterior side of the hinge.

When the toggle 138 is in any position such that it does not depress the button 106 (FIGS. 1, 2 and 3), the spring 124 (FIG. 5) urges the flexion stop 94 out of the recess 92. However, when the arms 22, 24 are at any angle of flexion greater than 10°, a medial surface of each arm 22, 24 maintains the flexion stop 94 within the recess 92 as shown in FIG. 2. The arms 22, 24 are thus freely rotatable between maximum flexion and 10° short of full extension. When the arms 22, 24 reach 10° short of full extension, the flexion abutment faces 50 on the arms clear the flexion abutment faces 116, 118 on the flexion stop 94, as shown in FIG. 3. The medial surfaces of the arms 22, 24 no longer maintain the flexion stop 94 within the recess 92. The spring 124 forces the flexion stop 94 out of the recess 92 until the lateral face 108 of the flexion stop 94 contacts a medial surface of the lateral bearing plate 38, as shown in FIG. 3. If a lateral bearing plate 38 is not provided, then the spring 124 forces the flexion stop 94 out of the recess 92 until the lateral face 108 of the flexion stop 94 contacts a medial surface of the second hinge plate 28.

Figure 8A:
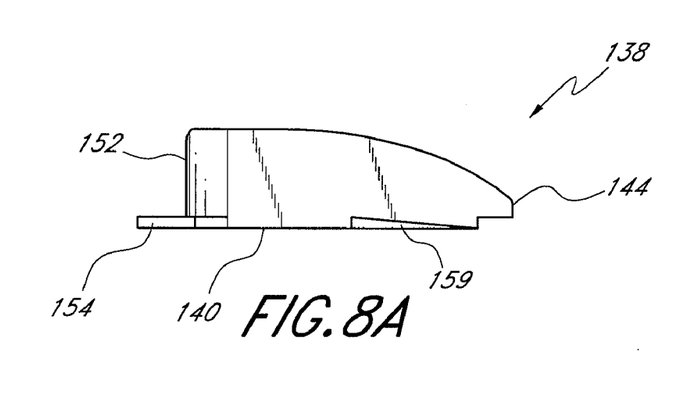
FIG. 8A is a bottom view of the toggle of the lockable hinge of FIG. 1.
Figure 8B:
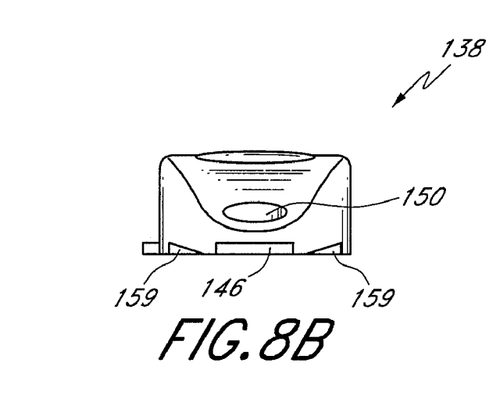
FIG. 8B is a rear view of the toggle of FIG. 8A.
Figure 8C:
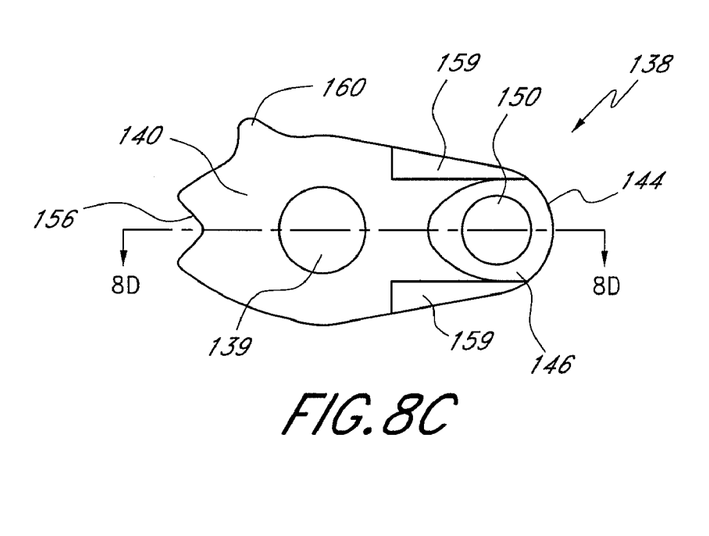
FIG. 8C is a side view of the toggle of FIG. 8A.
Figure 8D:
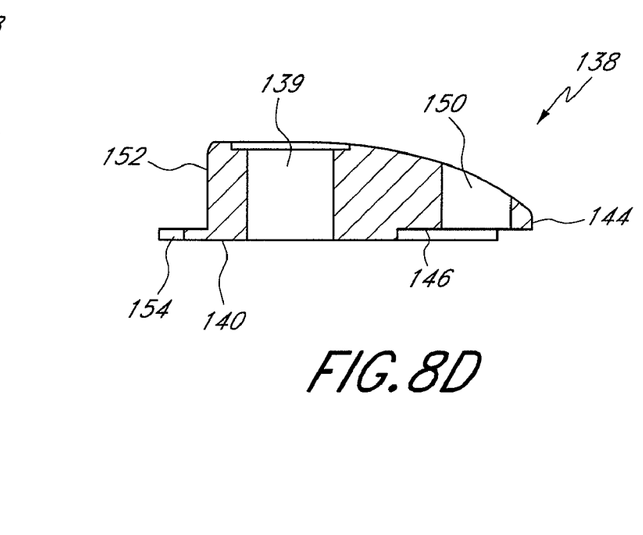
FIG. 8D is a bottom cross-sectional view of the toggle of FIG. 8C, taken along line 8D-8D.

Preferably a second end 152 (FIGS. 8A and 8D) of the toggle 138 opposite the first end 144 includes an extension 154 having a V-shaped indentation 156 (FIG. 8C). When the hinge 20 is in the locked mode, such that the toggle 138 does not depress the button 106 (FIGS. 1, 2 and 3), preferably the toggle 138 is oriented such that the toggle first end 144 is adjacent the anterior edge 62 of the second hinge plate 28 (FIG. 1). In this orientation, the crest 112 of the button 106 resides in the V-shaped indentation 156 on the second end 152 of the toggle 138, as shown in FIG. 1. The button 106 thus prevents the toggle 138 from rotating freely.

When the flexion stop 94 is in the position shown in FIG. 3, the flexion stop 94 limits flexion of the arms 22, 24 to 10°. The hinge 20 thus provides support for the wearer's knee, preventing him or her from flexing his or her knee more than 10°. The hinge 20 thus provides the benefits described above to patients with musculo-skeletal or neurological disorders. When the patient is ready to flex his or her knee, for example to sit down, he or she depresses the button 106 until the flexion stop 94 no longer interferes with the arms 22, 24. While holding the button 106 down, the patient is able to flex his or her knee.

If the patient wishes to lock the hinge 20 in the free range of motion mode of FIG. 4, he or she completely depresses the button 106 until the lateral end 148 (FIG. 7B) of the button 106 is substantially flush with the lateral face 142 of the second hinge plate 28. While holding the button 106 down, the patient rotates the toggle 138 into the locked position shown in FIG. 4. The button 106 lateral face pops up into the depression 146 on the toggle 138, locking the hinge 20 in the free range of motion mode. To disengage the button 106 from the toggle 138, the patient follows the procedure described above.

Figure 7B:
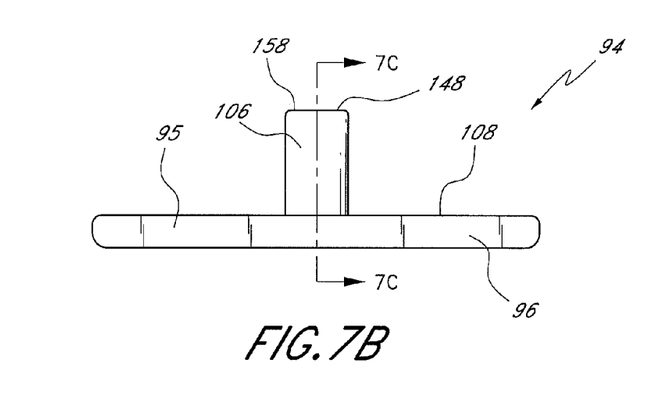
FIG. 7B is a rear view of the flexion stop of FIG. 7A.
Figure 7C:
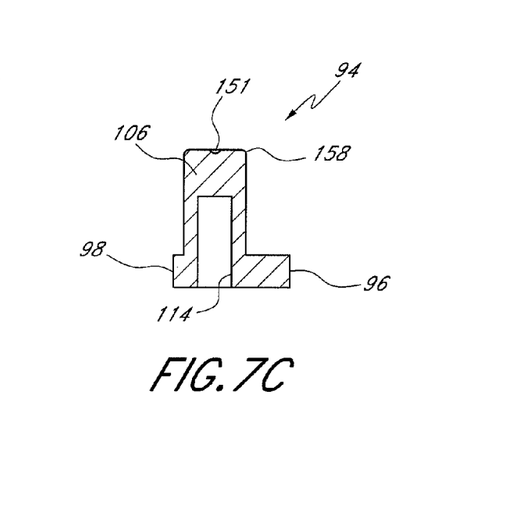
FIG. 7C is a bottom cross-sectional view of the flexion stop of FIG. 7B, taken along line 7C-7C.

To facilitate engaging and disengaging the button 106 with the depression 146, a perimeter of the lateral end 148 of the button 106 may include a chamfer 158 (FIGS. 7B and 7C). Similarly, an edge of the toggle adjacent the depression may include a sloped surface 159 (FIGS. 8A, 8B and 8C). As the toggle 138 nears the button lateral end 148, the sloped surface 159 engages the chamfer 158 and urges the button 106 toward the lateral face 142 of the second hinge plate 28. Thus, the wearer need not maintain the button lateral end 148 completely flush with the lateral face 142 of the second hinge plate 28. The wearer is thus able to lock the hinge 20 more easily. Those of skill in the art will appreciate that neither the chamfer 158 nor the sloped surface 159 is necessary to the proper functioning of the hinge 20.

A perimeter of the toggle 138 may include a pointer 160 (FIG. 8C), comprising a crest-shaped protrusion. The lateral face 142 of the second hinge plate 28 may include a locked symbol 162 and an unlocked symbol 164 (FIG. 1). When the toggle 138 is in the position of FIG. 4, wherein the toggle 138 first end covers the button 106 and the hinge 20 is in the free range of motion mode, the pointer 160 is positioned next to the unlocked symbol 164, indicating to the wearer that the hinge 20 is in the free range of motion mode. When the toggle 138 is in the position of FIGS. 1, 2 and 3, wherein the toggle first end 144 is positioned 180° from the button 106 and the hinge 20 is in the lockable mode, the pointer 160 is positioned next to the locked symbol 162, indicating to the wearer that the hinge 20 is in the locked mode. Those of skill in the art will appreciate that the locked and unlocked symbols 162, 164 and the pointer 160 are not necessary to the proper functioning of the hinge 20.

A knee brace including the present hinge 20 combines the support of a knee-immobilizing brace with the mobility of a fully flexible brace. With the hinge 20 in the locked mode of FIG. 4, a person suffering from any instability of the knee can wear the brace to assist him or her in standing and walking. When the person is ready to sit or lie down, he or she need not remove the brace in order to bend his or her knee. He or she simply depresses the button 106 while bending his or her knee. If the person wishes to lock the hinge in the free range of motion mode, for example, to participate in physical therapy, he or she depresses the button 106 and rotates the toggle 138 until it covers the button 106. When the person is ready to convert the hinge back to the locked mode, he or she inserts a slender object into the through-hole 150, depresses the button 106 and turns the toggle 138 until it no longer covers the button 106. Preferably the person rotates the toggle 138 to the position illustrated in FIGS. 1, 2 and 3 such that the button 106 engages the V-shaped indentation 156. The button 106 thus prevents the toggle 138 from rotating freely. By straightening his or her leg, the person rotates the arms 22, 24 such that the arms 22, 24 do not maintain the flexion stop 94 within the recess 92. The flexion stop 94 pops out of the recess, and the hinge 20 is in the locked mode. The brace thus provide support for standing and ambulation.

SCOPE OF THE INVENTION

The above presents a description of the best mode contemplated for carrying out the present lockable hinge, and of the manner and process of making and using it, in such full, clear, concise, and exact terms as to enable any person skilled in the art to which it pertains to make and use this lockable hinge. This lockable hinge is, however, susceptible to modifications and alternate constructions from that discussed above that are fully equivalent. Consequently, this lockable hinge is not limited to the particular embodiments disclosed. On the contrary, this lockable hinge covers all modifications and alternate constructions coming within the spirit and scope of the lockable hinge as generally expressed by the following claims, which particularly point out and distinctly claim the subject matter of the lockable hinge.

What is claimed is:

1. A lockable hinge for use in an orthopedic brace, the hinge comprising:
    a hinge plate;
    an arm rotatably mounted to the hinge plate, the arm being rotatable about a hinge axis; and
    a flexion stop; wherein
    the flexion stop is movable in a direction substantially parallel to the hinge axis between a first position in which the flexion stop limits a range of flexion of the arm, and a second position in which the flexion stop does not limit a range of flexion of the arm.

2. The lockable hinge of claim 1, further comprising a second arm rotatably mounted to the hinge plate, the second arm being rotatable about a second hinge axis.

3. The lockable hinge of claim 1, wherein when the arm occupies a first flexion range, the arm maintains the flexion stop in the second position.

4. The lockable hinge of claim 3, wherein when the arm occupies a second flexion range, the arm does not maintain the flexion stop in the second position.

5. The lockable hinge of claim 4, wherein when the arm occupies the second flexion range, a flexion abutment face on the arm cooperates with a flexion abutment face on the flexion stop to limit a range of flexion of the hinge.

6. The lockable hinge of claim 4, further comprising a toggle that is selectively engageable with the flexion stop.

7. The lockable hinge of claim 6, wherein when the toggle does not engage the flexion stop, the flexion stop moves toward the first position when the arm occupies the second flexion range.

8. The lockable hinge of claim 7, wherein when the toggle engages the flexion stop, the flexion stop remains in the second position when the arm occupies the second flexion range.

9. The lockable hinge of claim 1, further comprising an extension stop.

* * * * *